United States Patent [19]
Borggaard et al.

[11] Patent Number: 6,014,222
[45] Date of Patent: Jan. 11, 2000

[54] REFLECTION MEASURING DEVICE AND METHOD FOR DETERMINING QUALITY PROPERTIES OF ITEMS, PARTICULARLY FAT-CONTAINING ITEMS

[75] Inventors: Claus Borggaard, Viby Sj.; Allan J. Rasmussen, Fuglebjerg, both of Denmark

[73] Assignee: Slagteriernes Forskningsinstitut, Roskilde, Denmark

[21] Appl. No.: 09/155,527

[22] PCT Filed: Feb. 26, 1998

[86] PCT No.: PCT/DK98/00074

§ 371 Date: Sep. 24, 1998

§ 102(e) Date: Sep. 24, 1998

[87] PCT Pub. No.: WO98/38494

PCT Pub. Date: Sep. 3, 1998

[30] Foreign Application Priority Data

Feb. 28, 1997 [DK] Denmark .................. 0219/97

[51] Int. Cl.$^7$ .................. G01J 3/51; G01N 21/25; G01N 33/12
[52] U.S. Cl. .............. 356/419; 356/51; 250/339.11; 250/341.8; 250/910
[58] Field of Search ............ 356/51, 402, 407, 356/416, 419; 250/339.01, 339.05, 339.11, 341.8, 910

[56] References Cited

U.S. PATENT DOCUMENTS 4,583,858  4/1986  Lebling et al. .................. 356/402

5,745,229  4/1998  Jung et al. .................. 356/419

FOREIGN PATENT DOCUMENTS

| 0 402 877 | 12/1990 | European Pat. Off. |
| WO 87/05462 | 9/1987 | WIPO |
| WO 95/21375 | 8/1995 | WIPO |
| WO 97/24587 | 7/1997 | WIPO |

*Primary Examiner*—F. L. Evans

[57] ABSTRACT

A reflection measuring device for determining quality properties of items comprises a measuring head with a housing which is optically open in one side. The housing is designed to be placed on the item requiring measurement of the reflection factor, with the open side turned towards the surface of the item. The device has one or more light emitters arranged to illuminate the surface of the item adjacent to the open side of the housing, and a plurality of optical fibres, one end of which leads to the interior of the housing to receive light reflected from the surface of the item and to conduct it to a detection system. The system comprises filter elements each positioned adjacent to the other end of one or more of the optical fibres, each permitting passage of near infrared light in a predetermined wavelength range. Photodetectors each positioned by a filter element are arranged so as to measure the strength of the light passing through the filter. The photodetectors are each connected to an amplifier set to a predetermined amplification. The device is suitable for the on-line determination of the unsaturated fat content in the fatty tissue of carcasses or meat cuts conveyed on a slaughter or production line. On the basis of the unsaturated fat content, the device determines the consistency type of the fatty tissue (firm, normal or soft fatty tissue).

17 Claims, 1 Drawing Sheet

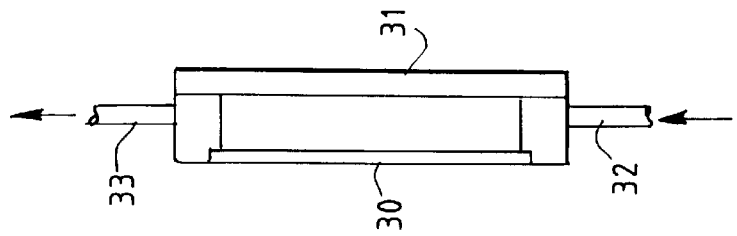
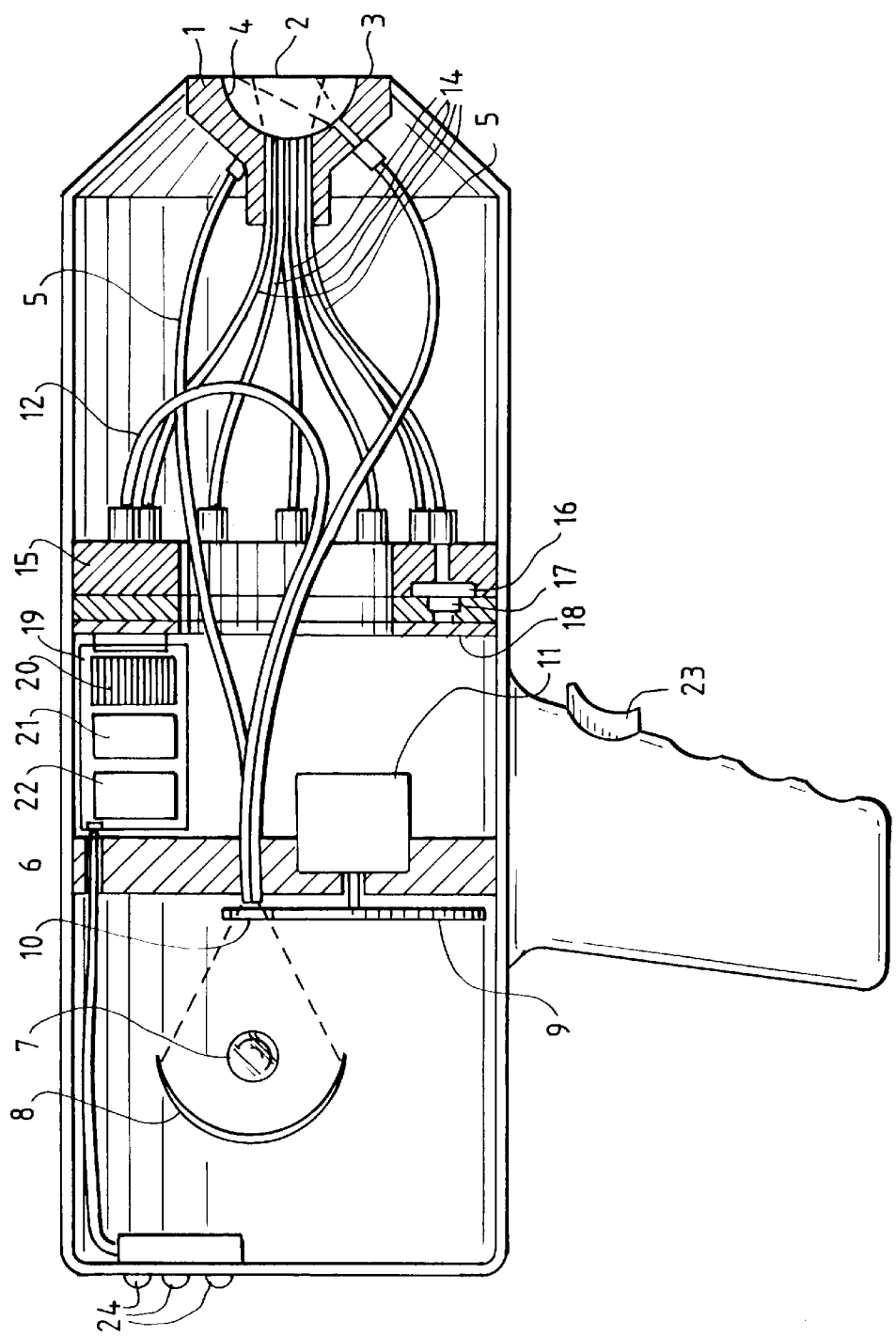

REFLECTION MEASURING DEVICE AND METHOD FOR DETERMINING QUALITY PROPERTIES OF ITEMS, PARTICULARLY FAT-CONTAINING ITEMS

The present invention relates to a reflection measuring device for determining quality properties of items, particularly fat-containing items, said device comprising a measuring head with a housing which is optically open in one side, the housing being designed to be placed on the item of which the reflection factor is to be measured, with the open side turned towards the surface of the item; one or more light emitters arranged to illuminate the surface of the item adjacent to the open side of the housing; a plurality of optical fibres, one end of which lead to the interior of the housing and has a distance from the housing's open side to receive light reflected from the surface of the item adjacent to the housing's open side and to conduct it to a detection system. The device is suitable for on-line determination of the contents of unsaturated fats in fatty tissue in carcasses or meat cuts conveyed on a slaughter or production line.

In certain productions various optical measuring devices are used at slaughterhouses or meat processing companies for determining the meat colour. For example, the colour may be measured with an insertion probe with a window in the side of the probe in which are located a light diode and a photodetector which measure the reflection factor of the meat outside the window. Another type of known device determines the meat colour from the visible surface of the item. This device includes a illumination arrangement for illuminating a part of the meat surface and a detector system for measuring the reflected light's strength and composition. There are also image-forming devices which measure the reflection factor at many points on the surface of the meat in order to obtain an image.

The contents of substances naturally occurring in meat, e.g. proteins or pigments, may also be a quality parameter. The substances contained may according to a known method be determined by spectrophotometric reflection measurement in the visible or infra-red region. An insertion probe may be used which has a fibre bundle for illuminating the meat adjacent to the probe window and a further fibre bundle for relaying the reflected light back to a spectrophotometer for measurement and analysis of the reflection spectrum. An analytical device is also known which measures the light transmission factor of a homogenised meat sample at various wavelengths. This device is able to determine the sample's contents of substances such as proteins, fat and water.

Cuts of meat, especially of pork and beef, often have a layer of fat as part of the product. The fat layer may have a varying consistency, which is unfortunate in cases where the consumer or user expect a firm consistency with clean and sharp cut edges, but instead is sometimes faced with uneven and irregular cut edges due to a soft consistency. A soft consistency is mainly due to the content of unsaturated fats in the fat layer (in the following called the fatty tissue).

Currently two different methods are known for detecting whether the fatty tissue is sufficiently firm. The first is to carry out a chemical analysis on a sample of the fatty tissue in order to determine the fat's iodine number. This will indicate how many unsaturated bonds the fat contains and is thus a measure of consistency. The analysis must be carried out in a chemical laboratory and is extremely time-consuming and labour intensive. The second method, which has found a certain application, consists of a trained operator marking the carcass or meat cut and carrying out a subjective assessment of the consistency of the fatty tissue. The material is thereby graded into three types: firm, normal and soft fatty tissue. The method can be carried out on-line on a company's slaughter or processing line. The method is unreliable owing to operator fatigue. In addition the meat is often not fully cooled at the time of assessment and this may lead to faulty grading, as consistency varies with the temperature of the material.

Generally, measuring devices are known which measure the surface colour of items. These devices include an illumination arrangement for illuminating the surface and a reflection measurement system with three channels for measurring in the blue, green and red regions. The devices may comprise a measuring head with a housing which is optically open in a side which is placed on the surface of the item.

The purpose of the present invention is to provide a device which is able to measure the surface of a carcass or meat cut on-line on the production line of slaughterhouses or meat processing companies, and which on the basis of the measurements is able automatically to determine the content of unsaturated bonds in the fats of the fatty tissue. Preferably, the device should be able to grade fatty tissue according to type (e.g. as firm, normal or soft fatty tissue), and it should be possible to carry out grading at least as reliably as when performed by a trained operator. Moreover, it should be possible to design the device as a measuring instrument which is easily portable and easily operated by an operator on the production line. Preferably, it should be possible to design the device as a portable pistol-like measuring instrument on which the sensor part requires merely to be placed on the surface of the fatty tissue.

This purpose is fulfilled by the device according to the invention.

The device according to the invention is characterised in that the detection system comprises:

filter elements each positioned adjacent to the other end of one or more of the optical fibres and each permitting passage of near infra-red light in a predetermined wavelength range, photodetectors each positioned by a filter element and arranged to measure the strength of the light passing through the filter, amplifiers each connected to a photodetector and each set to a predetermined amplification, the fibres, filter elements, photodetectors and amplifiers forming a number of channels through which optical and electrical signals pass from the light entry point in the fibres within the housing to the signal output of the amplifiers as separate analog signals, one or more A/D converters for converting the analog signals from the signal outputs of the amplifiers into equivalent digital signals and a calculation unit for processing the digital signals and converting them into an expression of a quality property of the item.

The device according to the invention thus comprises several channels for measurement of the reflection factor at various wavelengths in the near infra-red region and exploits the fact that materials display varying reflection factors at particular wavelengths in this region compared with their reflection factor at other wavelengths. (For example, fatty tissue in the infra-red region has a reflection factor which depends on the unsaturated fat content, and this fact can be exploited by the device to determine the consistency of the tissue). By designing the device's "spectrophotometer" as a number of analog fixed channels, each with its filter, photodetector and amplifier, a light-weight and robust measurement instrument is achieved which is easily carried and operated by an operator on the production line. The device is further notable for its particularly reliable results, due in part to the use of an individual amplifier for each channel (noise is reduced by using relatively long data capture periods and amplifiers adapted to the particular work area).

The device is thus particularly suited to routine on-line measurement in slaughterhouses, particularly for determining the quality of fatty tissue (firm, normal or soft consistency). It is significantly quicker than the known chemical analysis of fatty issue, and unlike the known subjective grading, the device according to the invention gives the same result even when the meat items are at varying temperatures. It can thus be used on the surface of pig and cattle carcasses being transported on a slaughter line still warm from slaughter.

One side of the housing is open or has a window. In the present, the terms "open side" or "opening" are most often used. These terms may, however, also include designs in which the side or opening has a transparent sheet or a transparent window or in which the interior of the housing is filled with a transparent material. These designs will be used especially to protect the light emitter and the end of the optical fibres leading to the housing from contamination.

The following gives preferred embodiments of the device according to the invention:

For each 20–100 nm in a range of the near infra-red region from 800–2400 nm, a filter element may be provided with a bandwidth of 20 nm or less.

Preferably, the device according to the invention includes 6–27 filter elements permitting the passage of light in the near infra-red region from 800–1800 nm. Preferably the elements have a bandwidth of 20 nm or less.

In addition to channels having the near infra-red filters mentioned, the device may have at least one channel with a filter element permitting the passage of light in the visible region. The measurement of the reflection factor in the visible region may for example be used to detect other properties of the item or to intercept sources of errors. So, for instance, the same device may be used to determine the consistency class of the fatty tissue and the colour class of the muscles, with the consistency determination function using the reflection factor measurement in the visible region to compensate for water on the surface of the item and the colour measurement function using the reflection factor measurements in the infra-red range to correct for the item's surface structure.

Said filter element permitting passage of light in the visible region has preferably a bandwidth of 100 nm or more. Preferably, the device includes three channels with filter elements permitting passage of light in the red, green and blue regions respectively.

Each photodetector, filter element and fibre end may be assembled into sets of units by means of a holder which encloses the filter and holds firm the detector and fibre end in a light-sealed manner. This provides a robust construction, especially if interference filters and Si or Ge photodiodes or transistors are used as the filter element and photodetector respectively.

The amplifiers may be operational amplifiers the amplification of which is set by means of resistors as a function of the channel's wavelength range.

Amplification may be so set that the signal obtained on the individual channels from measurement of a light reference plate is 80–95% of the amplifier's maximum signal.

There may be between 7 and 30 channels, each comprising a channel set consisting of fibres, a filter element, a photodetector and an amplifier, and at least one and preferably at most three filter elements will permit passage of light in the visible region and between 6 and 27 filter elements will permit passage of light in the near infra-red region. Although it is possible to use a greater number of channels, a relatively low number of near infra-red channels will suffice for most practical purposes, when account must also be taken of the device's weight and price.

The A/D converters can be arranged to read the analog signals from the amplifiers' outputs for a period of 0.1 to 1 second.

The light emitter may includes further optical fibres, one end of which, outside the housing, receive light from a lamp and the other end of which, leading to the housing, are at a distance from the open side of the housing and are directed at an inclined angle to the central area of the side. The fibres may be arranged to emit light in an angular region of between 25 and 65°. This makes it possible to take measurements over a relatively large area of the surface.

Between the lamp and the fibre end arranged to receive light from the lamp, a disk may be located which rotates by means of a motor and which is penetrated by slits at a distance from the disk edge which allow light to pass through the disk at determined angles of rotation, while blocking the passage of light between the lamp and the fibre ends at other angles of rotation. This permits a very rapid shift between measurements of light and darkness. Measurements of darkness are taken to compensate for false light straying into the interior of the housing and are also used to remove the parts of the signals which are due to the drift of the components (temperature, ageing).

The calculation unit may include an algorithm suitable to convert the digital signals which are obtained by measuring pork or beef with a fatty layer to an expression for the consistency of the fatty tissue.

The end of the fibre intended to receive reflected light may be directed towards the central area of the side, preferably at right angles to the side, and may be arranged to capture light in an angular region of between 25 and 65°. It is an advantage that the light is captured over a relatively large area of the surface to be measured, e.g. 1–10 cm$^2$, as local variations in the surface's reflection factor are thereby equalised.

The inside of the housing may be bulging, for instance taking the shape of a half-sphere. The opening or window in one side of the housing may have a transverse dimension of 1 to 5 cm. The distance from the light emitter in the housing to the opening or window may be 1 to 3 cm. The distance from the light entry end of the fibres to the opening or window may be 1 to 5 cm. This will permit a suitably large measurement area, thus equalising local variations.

The invention also relates to a method for determining quality properties of items by reflection measurement, wherein a measuring head with a housing which is optically open in one side is placed on the item of which the reflection factor is to be measured, with the open side turned towards the surface of the item; one or more light emitters illuminate the surface of the item adjacent to the open side of the housing; and a plurality of optical fibres, one end of which lead to the interior of the housing and has a distance from the housing's open side, receive light reflected from the surface of the item adjacent to the housing's open side and conduct it to a detection system.

The method is characterised in that the detection comprises:

filtering of the light by means of filter elements each positioned adjacent to the other end of one or more of the optical fibres and each allowing passage of near infra-red light in a predetermined wavelength range, measurement of the strength of the light passing through the filter by means of photodetectors each positioned by a filter element, amplification of the electrical signals of the photodectors by means of amplifiers each connected to a photodetector and each amplifying the signal by a predetermined factor, the optical and electrical signals passing from the light entry point of the fibres within the housing to the signal output of the amplifiers as analogs signals being separated from each others in channels each comprising one or more fibres, a filter element, a photodetector and an amplifier, conversion of the analog signals on the signal outputs into equivalent digital signals and processing of the digital signals and converting them into an expression of a quality property of the item.

An embodiment of the method is characterised in that measurements are performed at 6 to 27 wavelength ranges in the near infra-red region from 800 to 1800 nm by means of an equivalent number of filter elements, said elements preferably having a bandwidth of 20 nm or less.

Apart from the measurements in the near infra-red region measurements may be performed at at least one wavelength range in the visible region by means of at least one filter element allowing passage in the visible region.

The analog signals on the outputs of the amplifiers may be read for a period of 0.1 to 1 second.

For each channel in the infra-red region a plurality of readings may be performed while the housing is placed on the item, preferably between 100 and 10,000 readings per channel, the readings in each channel may be sorted in order of rising value of the digitalised signal, and the calculation unit may use the level at which the signal takes a stable maximum value as a basis for conversion to an expression for a quality property of the item.

Preferably, the amplification factor of each amplifier is set by means of fixed resistors which are selected such that the signal obtained from measurement of a light reference plate is 40 to 100% of the amplifier's maximum output signal.

In a preferred embodiment of the method according to the invention measurements are performed on pork or beef with a fat layer and the calculation unit converts the digital signals to an expression for the consistency of the fatty tissue using an appropriate algorithm.

It should be mentioned that the device according to the invention has been developed especially for quick and accurate determination of the consistency type of fatty tissue (firm, normal or soft consistency) and are therefore described herein with this application in mind. However, the device may be used in other areas within the meat industry, e.g. for determining the fat and protein contents of meat cuts or raw or processed meat products, such as minced or emulsified meat products (e.g. sausage filling). The colour of muscles or fatty tissue may be determined when using filters permitting passage of light in the visible region (which may be useful in the classification of cattle carcasses in particular).

In addition, the device according to the invention may be used within other areas of the food industry, such as in the dairy sector for determining the fat content and composition of milk and milk products or in the edible oil sector for determining oil type, iodine number and purity of cooking oil, edible oil or edible oil-based products, or in the grain and bakeries sector for determining the chemical composition of homogeneous or heterogeneous materials, or in the environmental sector, e.g. for monitoring or checking waste water, or in the chemicals and pharmaceuticals industry, such as for testing powder or liquids or for making diagnoses, e.g. on the basis of the reflection spectrum of the skin. The device according to the invention may in fact be used wherever advantage may be taken of the fact that the material under investigation has a varying reflection spectrum in the near infra-red region and where there is a need for quick and precise measurement with a portable instrument.

The invention is explained in greater detail in the following with reference to the drawings, in which FIG. 1 is a sectional view of a measuring pistol according to the invention for determining the consistency of fatty tissue, and FIG. 2 is a sectional view of a measuring cell for use in measuring liquid items in particular.

The measuring pistol (FIG. 1) includes a measuring head with a housing 1, which is open on one side 2 and on this side has a continuous edge 3 which is designed to lie against the surface of the fatty tissue during measurement. The inside 4 of the housing has the shape of a half-sphere with a diameter of 1.5 to 3 cm and is coloured black to minimise reflections from the wall.

Through the wall of the housing are inserted three optical fibres 5, of which only two are visible in FIG. 1. The ends of the fibres are directed towards the centre of the side or the circular area 2.

At their other end the fibres 5 are gathered into a fibre bundle 6, the end surface of which may be illuminated by a 6 W halogen lamp 7 with reflector 8. Between the lamp and the fibre bundle is positioned a disk 9, which at a distance from its edge is penetrated by holes 10 permitting the passage of light. Disk 9 is mounted on the shaft of a motor 11 and can thus be rotated during measurement. In certain positions the disk blocks off light from the lamp preventing the fibres from transmitting light into the interior of the housing 1. In other positions, the disk allows light to pass from lamp 7 to fibres 5, so that these transmit light into the interior of the housing. In operation there is an alternation between light and darkness 50–100 times per second. The angle of radiation of the fibre ends is between 40 and 50°, so that the area of the spot of light formed on the surface of a sample of fatty tissue is between 0.5 and 3 $cm^2$. The angle is shown in FIG. 1 by stippled lines.

The fibre bundle 6 also includes a fourth fibre 12, which is led round the measuring head and thence directly to a Si photodiode or transistor as a test of the light output of lamp 7.

A further fibre bundle is also led through the wall of housing 1. It is designed to capture light reflected from the surface of a sample in contact with the open side 2 of the housing. The fibres capture light over a angle of between 40 and 50°, as indicated by stippled lines in FIG. 1. The area of capture is essentially coincident with the spot of light originating from fibres 5.

Outside housing 1 the fibre bundle is divided at random into twelve single fibres or twelve groups of fibres 14, of which the ends are fixed in an annular holder 15. The end surfaces of fibres 14 are led to the side of individual interference filters 16. Three of the twelve filters are of broad bandwidth and allow passage of light in the red, green and blue spectral regions (x,y,z filters). The remaining nine filters are all of small bandwidth with a bandwidth of approx. 1% of the median wavelength. They permit passage of near infra-red light in nine preselected ranges between 800–1800 nm. On the opposite side of each filter 16 is positioned a photodiode or phototransistor 17 of Si or Ge type. Si photodiodes/transistors are used for filter wavelengths under 1100 nm and Ge photodiodes/transistors are used for filter wavelengths over 1100 nm. The electrical connections of the diodes/transistors are soldered to conductors on a circuit board 18. The holder 15 therefore contains twelve filters 16 and diodes/transistors 17. It also contains the photodiode/transistor which receives light from fibre 12.

On a circuit board 19, shown schematically, there are mounted thirteen operational amplifiers 20, each of which are connected to a photodiode/transistor 17 (i.e. the twelve photodiodes/transistors receiving light from fibres 14 and the photodiode/transistor which receives light from fibre 12). The amplification of each amplifier is set by fixed resistors and is selected such that the signal obtained from measurement of a light reference plate is approx. 90% of the amplifier's maximum output signal. The amplification of each amplifier can be adjusted in steps of 6 dB over a 100 dB range. When a measurement is taken of a light reference plate, the weakest signal on an amplifier input will be more than 20 times weaker than that on the amplifier with the strongest input signal (apart from the amplifier connected to the Si photodiode/transistor which receives light from fibre 12). This is due in part to the different damping of the filters and to the wavelength-dependent sensitivity of the diodes. This variation is compensated by individually setting the amplification of each amplifier.

The analog outputs of the amplifiers are each connected to an input on a multi-channel A/D converter 21 mounted on the circuit board 19. The resolution of the converter is 16 bits. The converter takes 1000–2000 readings per second on each channel, including both light measurements and darkness measurements (i.e. when the disk 9 is blocking out the light). The circuit board also carries a microprocessor 22 for data processing and memory units for storage of measuring programs and volatile measuring data.

One input on the processor is connected to a switch which can be activated by a control button 23 in the handle of the measuring pistol. The processor also has outputs which can switch on and off three photodiodes 24 or control an alphanumeric display for reading off by the operator.

It is evident that the processor 22 and memory units may be located in a unit other than the measuring pistol, e.g. in a main computer, so as to make measuring data and results easily accessible for others apart from the operator and/or for use in the control or automatic sorting of meat items. Another possibility is an arrangement whereby the pistol transmits data and results to a network where they are accessible to users and equipment.

The measuring pistol is used in the following manner:

The operator applies the measuring head of the pistol to the surface of the item requiring classification of fat quality, and activates control button 23. This initiates a measuring program stored in a memory unit which can be read by the microprocessor. The processor reads and interprets the digital signals from the A/D converter, which are an expression of the light absorption of the item at the filters' different wavelengths. Data capture lasts 0.5 to 1 second, after which the operator may remove the pistol from the item. During this time between 700 and 1400 readings per channel are taken. For each channel the readings are sorted in order of rising value of the digitalised signal and the processor determines the level at which the signal takes on a stable minimum value and the level at which a stable maximum value is assumed. These correspond respectively to the value of the cleaned darkness signal and the value of the cleaned light signal. By means of these values and the light and darkness values of the reference channel, the reflection factor of the item is calculated in twelve different wavelength ranges.

The system, which comprises separate measuring channels, has extremely low noise. When measurement is made on a white reference plate the noise is below 0.01% absolute on any of the channels. When a measurement is made on back fat (which has a far lower reflection factor) noise is below 0.1% absolute on any of the channels.

On the basis of the cleaned light and darkness signal values and previously stored information, the processor calculates automatically the fat consistency type of the item in question. The result is displayed to the operator by lighting one of the light diodes 24, e.g. a green light for firm fatty tissue, a yellow light for normal consistency and a red light for soft tissue.

On the basis of the indications provided by the diodes, the operator can sort the items by fatty tissue quality, e.g. by sending meat with firm fatty tissue consistency for special productions, while sending other meats for normal production.

The measuring pistol has been used for measuring 60 cold back fat samples (temperature 0–10° C.) and 60 back fat samples warm from slaughter (temperature 23° C.). The samples were previously assessed by a trained operator. The selection of samples was such that in the judgement of the operator there were an equal number of fat samples with a firm consistency as there were with a soft consistency. The measuring pistol graded 115 of the 120 samples in the same way as the operator. Examination of the results of the five samples graded differently by the operator and the measuring device showed that all were on the borderline between soft and firm. The measuring device is thus able to determine the consistency type with at least the same reliability as a trained operator.

A glass disk (a window) was mounted in the open side 2 of the housing to prevent contamination of the interior of the housing when measuring extremely soft items. The disk was positioned such that its outer side was flush with edge 3. The data processing program as also changed. This modified measuring pistol was used to measure 11 samples of minced or homogenised meat with a fat content varying from 1 to 10% by weight. The results showed that the measuring device predicts fat content with an accuracy greater than 1% absolute. On a colour scale of six steps, the measuring device was able to predict the colour class of minced meat with extremely high reliability.

FIG. 2 shows a measuring cell for use with the measuring pistol in FIG. 1. The cell includes a box-shaped chamber of which one wall is a glass sheet 30. Opposite this wall is another wall 31 made from a white material, e.g. plastic. In the walls connecting the two walls is a pipe 32 for feeding fluid into the chamber and another pipe 33 for removing fluid from the chamber. If it is desired to determine the optical properties of a fluid, this fluid is fed into the chamber expelling all the air. The measuring pistol according to FIG. 1 (with an adapted data processing program) is then brought with its measuring head onto glass sheet 30 and control button 23 is activated. This initiates a measurement of the reflection factor of the fluid at various wavelengths. If the fluid is transparent the light is reflected on the white wall 31.

Measurements have been carried out on nine types of cooking oil with different contents of unsaturated fats. The measuring pistol was able to differentiate all nine types. In another series of experiments, the pistol proved able to distinguish salmon oil, cod liver oil, corn oil, melted pork fat from soft fatty tissue and melted pork fat from firm fatty tissue.

The pistol was also able to identify at least 10–15 different steps in a mixture series of paraffin oil (iodine number=0, saturated fatty acid) and cooking oil with a high content of linolenic acid (high iodine number, polyunsaturated fatty acid). The series varied from pure paraffin to pure cooking oil.

The pistol is thus also suitable for quickly differentiating between different materials and for determining the mixture ratio between two or even more materials.

It may be necessary to alter the wavelength ranges of the filters (change the filters) when the pistol is used for other types of measurements than it was originally designed for. In the case of the twelve-channel pistol described, however, it is possible to distinguish both the consistency type of the fatty tissue and the colour of the meat muscles with the same set of filters. This is due particularly to the fact that the pistol contains both filters in the near infra-red region (800–2400 nm) and filters in the visible region (400–700 nm).

We claim:

1. A reflection measuring device for determining quality properties of items, said device comprising: a measuring head with a housing which is optically open in one side, said housing being designed to be placed on the item from which the reflection factor is to be measured; one or more light emitters arranged to illuminate the surface of the item adjacent to the open side of the housing; a plurality of optical fibres, one end of which lead to the interior of the housing and lie a distance from the housing's open side to receive light reflected from the surface of the item and to conduct it to a detector system, said detector system comprising: a plurality of filter elements each positioned adjacent to the other end of one or more of the optical fibres and each allowing passage of near infra-red light in a predetermined wavelength range; a plurality of photodetectors each positioned by a filter element and arranged so as to measure the strength of the light passing through the filter element; a plurality of amplifiers each connected to a photodetector and each set to a predetermined amplification, the optical fibres, filter elements, photodetectors and amplifiers forming a plurality of channels through which optical and electrical signals pass from the light entry point in the fibres within the housing to the signal output of the amplifiers as separate analog signals; one or more A/D converters for converting the analog signals from the signal outputs of the amplifiers into equivalent digital signals; and a calculation unit for processing the digital signals and converting them into an expression of a quality property of the item.

2. A device according to claim 1, wherein the detector system includes between 6–27 filter elements allowing passage of light in the near infra-red region from 800 to 1800 nm, said filter elements preferably having a bandwidth of 20 nm or less.

3. A device according to claim 1, wherein the detector system in addition includes at least one channel with a filter element which allows passage of light in the visible region.

4. A device according to claim 3, wherein the filter element allowing passage of light in the visible region has a bandwidth of 100 nm or more.

5. A device according to claim 1, wherein each photodetector, filter element and end of one or more optical fibres is assembled into sets of units by means of a holder which encloses the filter element and holds firm the photodetector and fibre end in a light-sealed manner.

6. A device according to claim 3, wherein the detector system includes between 7 and 30 channels each comprising a channel set consisting of one or more optical fibres, a filter element, a photodetector and an amplifier, at least one and at most three filter elements permit passage of light in the visible region and between 6 and 27 filter elements permit passage of light in the near infra-red region.

7. A device according to claim 1, wherein the A/D converters are arranged to read the analog signals from the outputs of the amplifiers for a period of 0.1 to 1 second.

8. A device according to claim 1, wherein the light emitter includes further optical fibres one end of which lie outside the housing and receive light from a lamp, and the other end of which lead to the housing and lie at a distance from the open side of the housing at an inclined angle to the central area of the side, said fibres being arranged to emit light in an angular range of between 25 and 65°.

9. A device according to claim 8, wherein a disk is positioned between the lamp and the fibre end arranged to receive light from the lamp, said disk being rotatable by means of a motor and being penetrated by slits at a distance from an edge of the disk, said slits allowing light to pass through the disk at certain angles of rotation while the passage of light is blocked between the lamp and the fibre end at other angles of rotation.

10. A device according to claim 1, wherein the calculation unit includes an algorithm suitable to convert digital signals which are obtained by measurement of pork or beef with a fat layer to an expression for consistency of the fatty tissue.

11. A method for determining quality properties of items by reflection measurement, wherein a measuring head with a housing which is optically open in one side is placed on the item from which the reflection factor is to be measured, with the open side turned towards the surface of the item; wherein one or more light emitters illuminate the surface of the item adjacent to the open side of the housing; and wherein a plurality of optical fibres, one end of which lead to the interior of the housing and lie a distance from the housing's open side, receive light reflected from the surface of the item adjacent to the housing's open side and conduct it to a detection system, said method comprising the steps of:

(a) filtering of the light by means of filter elements each positioned adjacent to the other end of one or more of the optical fibres and each allowing passage of near infra-red light in a predetermined wavelength range, (b) measuring the strength of the light passing through the filter by means of photodetectors each positioned by a filter element, (c) amplifying the electrical signals of the photodetectors by means of amplifiers each connected to a photodetector and each amplifying the signal by a predetermined factor, the optical and electrical signals passing from the light entry point of the fibres within the housing to the signal output of the amplifiers as analogs signals being separated from each others in channels each comprising one or more fibres, a filter element, a photodetector and an amplifier, (d) converting the analog signals on the signal outputs into equivalent digital signals, (e) processing of the digital signals and converting them into an expression of a quality property of the item.

12. A method according to claim 11, wherein measurements are performed at 16–27 wavelength ranges in the near infra-red region from 800 to 1800 nm by means of an equivalent number of filter elements.

13. A method according to claim 11, wherein measurements in addition are performed at at least one wavelength range in the visible region by means of at least one filter element allowing passage in the visible region.

14. A method according to claim 11, wherein the analog signals on the outputs of the amplifiers are read for a period of 0.1 to 1 second.

15. A method according to claim 11, wherein a plurality of readings are performed for each channel in the infra-red region while the housing is placed on the item, and wherein the readings in each channel are sorted in order of rising value of the digitalised signal, and wherein the level at which the signal takes a stable maximum value is used as a basis for conversion to an expression for a quality property of the item.

16. A method according to claim 11, wherein the amplification factor of each amplifier is set by means of fixed resistors which are selected such that the signal obtained from measurement of a light reference plate is 40 to 100% of the amplifier's maximum output signal.

17. A method according to claim 11, wherein measurements are performed on pork or beef with a fat layer and wherein the digital signals are converted to an expression for the consistency of the fatty tissue using an appropriate algorithm.

* * * * *

UNITED STATES PATENT AND TRADEMARK OFFICE
CERTIFICATE OF CORRECTION

PATENT NO. : 6,014,222
DATED : January 11, 2000
INVENTOR(S) : Claus Borggaard and Allan J. Rasmussen It is certified that error appears in the above-indentified patent and that said Letters Patent is hereby corrected as shown below:

In Claim 12, line 2, delete "16" and substitute —6—.

Signed and Sealed this

Seventeenth Day of October, 2000

Attest:

Q. TODD DICKINSON

*Attesting Officer*   *Director of Patents and Trademarks*